United States Patent
Gerber et al.

(12)

(10) Patent No.: US 6,360,750 B1
(45) Date of Patent: Mar. 26, 2002

(54) MINIMALLY INVASIVE SURGICAL TECHNIQUES FOR IMPLANTING DEVICES THAT DELIVER STIMULANT TO THE NERVOUS SYSTEM

(75) Inventors: Martin Theodore Gerber, Maple Grove, MN (US); Michael C. Sherman, Memphis, TN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 09/489,544

(22) Filed: Jan. 21, 2000

Related U.S. Application Data (63) Continuation of application No. 09/301,937, filed on Apr. 29, 1999, now Pat. No. 6,055,456.

(51) Int. Cl.$^7$ .............................. A61B 17/02; A61N 1/05
(52) U.S. Cl. ...................... 128/898; 623/902; 607/118; 600/201; 600/377; 600/207
(58) Field of Search .................... 128/898; 623/902; 600/235, 377, 104, 135, 201, 207; 604/891.1; 607/41, 115–118

(56) References Cited

U.S. PATENT DOCUMENTS

| | | | |
|---|---|---|---|
| 4,771,779 A | | 9/1988 | Tanagho et al. ............. 128/419 |
| 5,571,156 A | * | 11/1996 | Schmukler ................... 607/116 |
| 5,855,594 A | * | 1/1999 | Olive et al. .................... 607/28 |
| 5,967,970 A | * | 10/1999 | Cowan et al. ............... 600/207 |
| 6,055,456 A | * | 4/2000 | Gerber ........................ 607/117 |

\* cited by examiner

*Primary Examiner*—Corrine McDermott
*Assistant Examiner*—Choon P. Koh
(74) *Attorney, Agent, or Firm*—Banner & Witcoff, Ltd.

(57) ABSTRACT

Devices are currently implanted in patients to treat pain and other conditions including incontinence by delivering stimulants to the nervous system. Surgical methods are improved for implanting the devices. The soft tissues of the body are dilated above the site of device implantation, for example, above the sacrum, to create an annulus of dilated soft tissues. The tissues are dilated by introducing into the soft tissue sequentially larger cannulated dilating devices. A tubular retractor is then passed over the largest introduced dilating device and at least a number of the dilating devices are retracted. This establishes a tubular device insertion corridor through the dilated soft tissues to the site of implantation, for example, the foramen of the sacrum. The device to be implanted, such as an electrical lead, is then inserted through the corridor. The device is tested in situ. Finally, such other method steps are performed, including closing the corridor, as implantation requires. As preferred, when establishing a corridor through the tissues, a corridor is established sufficient in size for insertion of an endoscope; and the endoscope is inserted and utilized for visual imaging as needed. Also as preferred, the nervous system of the body is tested for appropriate reaction to the stimulant through insertion and manipulation of testing implements through the corridor before performing other method steps. As further preferred, the device to be implanted is anchored through insertion and manipulation of anchoring implements through the corridor. The device is also connected to associated equipment, such as an implantable pulse generator, by tunneling through the soft tissues and passing an extension, a cable, from the lead to the site of implantation of the other equipment, such as in the abdomen.

15 Claims, 5 Drawing Sheets

MINIMALLY INVASIVE SURGICAL TECHNIQUES FOR IMPLANTING DEVICES THAT DELIVER STIMULANT TO THE NERVOUS SYSTEM

This is a continuation application of Ser. No. 09/301,937, filed Apr. 29, 1999, Now U.S. Pat. No. 6,055,456.

BACKGROUND OF THE INVENTION

This invention relates to surgical methods of implanting leads for electrical stimulation and drug delivery therapies to the spinal cord and peripheral nervous system. More specifically, the invention relates to such surgical implant methods directed to leads for sacral nerve stimulation.

Pain

Briefly, the brain, not the point of an injury, registers any sensation of pain. When pain is felt, it is a reaction to signals that are transmitted throughout the body. These signals are sent from the pain source, through the nerves in the spinal cord, to the brain, where they are perceived as pain. Pain can be controlled by preventing the pain signals from reaching the brain. If the pain signals never reach the brain, pain is not felt.

The origin of some pain is neuropathic, while other pain is nociceptive. This is important to know because different treatments will work better for each type of pain. Neuropathic pain is pain that is caused by damage to nerve tissue. It is often felt as a burning or stabbing pain. One example of a neuropathic pain is a "pinched nerve." Nociceptive pain means pain caused by an injury or disease outside the nervous system. It is often an on-going dull ache or pressure, rather than the sharper, trauma-like pain more characteristic of neuropathic pain. Examples of chronic nociceptive pain include pain from cancer or arthritis. Some people experience mixed pain, which is a combination of neuropathic and nociceptive pain.

Acute pain (such as spraining an ankle) acts as a warning to signal harm or possible damage to tissues in the body. It prevents additional damage by alerting you to react and remove the source of pain. However, when pain lasts a long time (over six months) and is not relieved by standard medical management, it is called "chronic" pain. In chronic pain, the pain signal no longer helps, but hinders the body. Chronic pain may result from a previous injury long since healed. Or it may have an ongoing cause, such as arthritis, cancer, nerve damage, or chronic infection. With chronic pain, normal lifestyles can be restricted or even impossible. Many people suffer with chronic pain, unaware that there are a variety of treatment options that can help them live more normal lives. If a person has chronic pain, that person should seek out information about these various treatment options. Because there are many new ways to treat pain, it is important that patients speak openly with their doctors or with doctors who specializes in treating chronic pain—pain specialists.

Pain is recognized as a major public health problem. In the United States, it is estimated that chronic pain affects 15% to 33% of the U.S. population, or as many as 70 million people. In fact, chronic pain disables more people than cancer or heart disease and costs the American people more than both combined. Pain costs an estimated $70 billion a year in medical costs, lost working days, and workers' compensation.

Many people with chronic pain do not seek pain relief, or even tell their doctors about their pain. Most often, the reasons for keeping pain a secret are based on fears or myths: (1) Fear of being labeled as a "bad patient." A patient will not find relief if he or she does not speak with a doctor about pain. (2) Fear that increased pain may mean that the disease has worsened. Regardless of the state of disease, the right treatment for pain may improve daily life for the patient and the involved family. (3) Fear of addiction to drugs. Research has shown that the chance of people with chronic pain becoming addicted to pain-relieving drugs is extremely small. When taken properly for pain, drugs can relieve pain without addiction. Needing to take medication to control pain is not addiction. (4) Lack of awareness about pain therapy options. Honesty about how pain feels and how it affects life is required. Inquires are appropriate about the pain therapy options that are available. Often, if one therapy is not effectively controlling pain, another therapy can. (5) Fear of being perceived as "weak." Some believe that living stoically with pain is a sign of strength, while seeking help often is considered negative or weak. This perception prevents them seeking the best treatment with available therapies. Fears and misconceptions should not keep patients from talking to doctors and other members of health care teams about getting adequate pain relief. Help and relief are possible, but only if symptoms are discussed with a doctor.

Advanced Pain Therapies

APT Neurostimulation ("Advanced Pain Therapy Neurostimulation") is available from Medtronic, Inc., and commonly used for neuropathic pain. APT Intrathecal treatment, also available from Medtronic, Inc., is commonly used for nociceptive pain.

APT Neurostimulation (including both spinal cord stimulation and peripheral nerve stimulation) uses a small neurostimulation system that is surgically placed under the skin to send mild electrical impulses to the spinal cord. The electrical impulses are delivered through a lead (a special medical wire) that is also surgically placed. These electrical impulses block the signal of pain from reaching the brain. Peripheral nerve stimulation works in the same way, but the lead is placed on the specific nerve that is causing pain rather than the spinal cord. Because APT Neurostimulation works in the area where pain signals travel (the spinal cord or specific nerve), electrical impulses (which are felt as tingling) can be directed to cover the specific sites where pain is felt. APT Neurostimulation can give effective pain relief and decreases the need for pain medications. In addition, APT Neurostimulation is reversible and non-destructive. A doctor can do a screening test, which helps predict whether the therapy will relieve pain. Typically patients who have success with APT Neurostimulation experience a 50%–70% reduction in their pain and improved ability to go about daily activities.

There are two types of Medtronic Neurostimulation systems: (1) A totally implantable system: The Itrel® 3 system includes an implantable pulse generator (IPG), a patient programmer, and an extension and lead(s); and (2) A radio frequency system: The Mattrix® system comprises an external transmitter, an antenna, an implanted receiver, and lead(s). The main difference between the two systems is the battery location. The totally implantable system uses a battery that is placed beneath the skin—no part is outside the body. The patient and the doctor can control the totally implantable system with an external programmer. The radio frequency system uses a battery that is worn outside the body. This system requires the patient to wear an antenna on the skin over the site of the receiver. Approximately 90% of people currently receiving APT Neurostimulation use totally implantable systems.

In the totally implantable system, the implantable pulse generator (IPG) sends precise, electrical pulses to your spinal cord to control pain. The IPG contains a special battery and electronics to create these pulses. The system, which is about 2.25 inches (6 cm) across, less than one-half inch (1 cm) thick and about 2 inches (5.2 cm) high, is most often placed under the skin of the abdomen. The lead is a small medical wire with special insulation. It is placed next to the spinal cord through a needle and contains a set of electrodes (small electrical contacts) through which electrical stimulation is delivered to the spinal cord. This stimulation is often described as tingling. The extension is a small cable about 20 inches (50 cm) long that is placed under the skin and connects the lead to the IPG.

The doctor or a nurse can use an additional programmer to adjust the APT Neurostimulation system so that it most effectively treats pain. This programmer includes a computer, programming head, and a printer. The programming head is placed over the IPG to program the settings using radio waves. This procedure is done through the skin and is painless. There is also a patient programmer, a hand-held device that allows the patient to change or control his or her own stimulation. The patient programmer allows the patient to adjust the stimulation using painless radio waves between visits to the doctor.

APT Intrathecal uses a small pump that is surgically placed under the skin of the abdomen to deliver medication directly into the intrathecal space (where fluid flows around the spinal cord). The medication is delivered through a small tube called a catheter that is also surgically placed. The spinal cord is like a highway for pain signals on their way to the brain, where the feeling of pain is experienced by the body. Because the medication goes directly to the site of action in the spinal cord, where pain signals travel, APT Intrathecal offers many people significant pain control with much lower doses of medication than would be required by oral medications (pills). This helps minimize the side effects that often accompany other treatments.

A doctor can do a screening test to see if APT Intrathecal will relieve pain, before the patient commits to the therapy. In addition, APT Intrathecal is non-destructive and reversible. Typically, people who have success with APT Intrathecal experience greater than 50% reduction in their pain and improved ability to go about activities of daily living.

The SynchroMed® Infusion System is the fully implantable, programmable system available from Medtronic. The SynchroMed Infusion System has two parts that are both placed in the body during a surgical procedure: the catheter and the pump. The catheter is a small, soft tube. One end is connected to the catheter port of the pump, and the other end is placed in the intrathecal space (where fluid flows around the spinal cord). The pump is a round metal device that stores and releases prescribed amounts of medication directly into the intrathecal space. It is about one inch (2.5 cm) thick, three inches (8.5 cm) in diameter, and weighs about six ounces (205 g). It is made of titanium, a lightweight, medical-grade metal. The reservoir is the space inside the pump that holds the medication. The fill port is a raised center portion of the pump through which the pump is refilled. The doctor or a nurse inserts a needle through the patient's skin and through the fill port to fill the pump. Some pumps have a side catheter access port that allows the doctor to inject other medications or sterile solutions directly into the catheter, bypassing the pump.

The SynchroMed pump automatically delivers a controlled amount of medication through the catheter to the intrathecal space around the spinal cord, where it is most effective. The exact dosage, rate and timing prescribed by the doctor are entered in the pump using a programmer, an external computer-like device that controls the pump's memory. Information about the patient's prescription is stored in the pump's memory. The doctor can easily review this information by using the programmer. The programmer communicates with the pump by radio signals that allow the doctor to tell how the pump is operating at any given time. The doctor also can use the programmer to change your medication dosage.

Relief for Bladder Control Problems

In addition to treating pain, Medtronic devices assist patients with other concerns. The Medtronic InterStim® Therapy for Urinary Control offers an approach for managing urinary urge incontinence, nonobstructive urinary retention, and significant symptoms of urgency-frequency in patients who have failed or could not tolerate more conservative treatments. Millions of people of all ages suffer from urinary urge incontinence, nonobstructive urinary retention, or significant symptoms of urgency-frequency. Individuals with these conditions often face debilitating challenges in their everyday lives. They can be preoccupied with trips to the bathroom, fears of embarrassment, and sleepless nights. Many sufferers become so anxious that they become isolated and depressed. There are limited treatment options to help relieve these symptoms. More conservative treatments include behavioral techniques (healthy lifestyle habits, diet modification, etc.) and medications (anticholinergics, antispasmodics, antimuscarinics, or tricyclic antidepressants).

The implantable InterStim Therapy system uses mild electrical stimulation of the sacral nerves (in the lower region of the spine) that influence the behavior of the bladder, sphincter, and pelvic floor muscles. In properly selected patients, InterStim Therapy can dramatically reduce or eliminate symptoms. As with APT Neurostimulation, a lead is surgically implanted, an extension runs to a neurostimulator, and the neurostimulator acts as an IPG to send precise, electrical pulses to your sacral nerves to control the treated symptoms. As with APT, Neurostimulation, the IPG contains a special battery and electronics to create these pulses. The system, which is about the same size, is most often placed under the skin of the abdomen. The lead again is a small medical wire with special insulation. It is anchored to the sacrum near the sacral nerves and contains a set of electrodes (small electrical contacts) through which electrical stimulation is delivered. This stimulation is often described as tingling. The extension again is a small cable between 4 and 20 inches long that is placed under the skin and connects the lead to the IPG. Treatment is non-destructive and reversible.

Current Surgical Lead Implantation Methods

As referenced above, for APT Neurostimulation and APT Intrathecal therapies, leads are placed next to the spinal cord inside the spinal column through needles. The body is opened to the spinal cord through open surgery. For Medtronic InterStim® Therapy for Urinary Control, leads are placed through the dorsal (back) surface of the sacrum, the bone above the coccyx (tailbone) and below the last vertebrae, that forms the dorsal wall of the pelvis. Leads are placed adjacent the sacral nerves as they transition through the posterior sacral foramina. The body is opened to the sacrum surgically. An incision is made through the skin, fascia, and paraspinal muscle fibers. The sacral foramina (foramen) are exposed, preserving the periosteum. The response of the foramen to stimulation is tested by a foramen needle. Once response is confirmed, the needle is retracted. The lead is inserted into the foramen to a depth of 1.0–1.5 inches in the usual case. A lead anchor is brought into contact with the periosteum, and the lead tested on its various electrodes for desired motor response. Once the desired response is observed, the lead is anchored by suturing the lead anchor to the sacral bone or periosteum. The fascia of the sacral incision is closed. A tunneling tool is then used to tunnel from the sacral site to a flank site (for abdominal IPG placement) and the extension is placed to extend from the lead to the IPG.

U.S. Pat. No. 4,771,779 issued on Sep. 20, 1998 to Tanahgo et al. for a System for Controlling Bladder Evacuation is incorporated by reference. U.S. patent application Ser. No. 09/301,937 filed on Apr. 29, 1999 by Gerber for a Single and Multi-Polar Implantable Lead for Sacral Nerve Electrical Stimulation is also incorporated by reference.

SUMMARY OF THE INVENTION

A primary object of the invention is to substantially advance the surgical methods employed for placing leads in the human body for spinal cord and peripheral nerve stimulation, including sacral nerve stimulation, and for placing catheters in the intrathecal space around the spinal cord for medication delivery.

Another primary object is to minimize the invasive nature, incision size and tissue disruption of current methods for placing leads in the human body for spinal cord and peripheral nerve stimulation, including sacral nerve stimulation, and for placing catheters in the intrathecal space around the spinal cord for medication delivery.

Other primary objects include substantially reducing the recovery times for surgeries as described, substantially reducing the lengths of hospital stays for such procedures, and substantially reducing risks of infection from such surgeries, while maintaining the substantial benefits that flow from the implantations for which the surgeries are needed.

In a first aspect, then, the invention includes an improvement in a surgical method for implanting a device in a living body for delivering a stimulant to the nervous system of the body. The improvement comprises several steps as follows. The soft tissues of the body are dilated at a site of device implantation to create an annulus of dilated soft tissues. The tissues are dilated through the introduction into the soft tissue of sequentially larger cannulated dilating devices, ending in a largest introduced dilating device. A tubular retractor is then passed over the largest introduced dilating device and at least a number of the dilating devices are retracted. This establishes a tubular device insertion corridor through the dilated soft tissues to the site of device implantation. The device to be implanted is then inserted through the operative corridor to the site of device implantation. The device is tested substantially in situ. Finally, such other method steps are performed, including closing the device insertion corridor, as the implantation of the device requires. As preferred, during the practice of the method, all the dilating devices are retracted; when establishing a tubular device insertion corridor through the dilated tissues to the site of device implantation, a corridor is established sufficient in size for insertion of an endoscope to the site of device implantation, and the endoscope is inserted and utilized for visual imaging as needed during the method. Also as preferred, the nervous system of the body is tested for appropriate reaction to the stimulant through insertion and manipulation of testing implements through the corridor before testing the device and before performing other method steps. As further preferred, the device to be implanted is anchored at the site of device implantation through insertion and manipulation of anchoring implements through the corridor before closing the corridor.

In another principal aspect, the invention is directed specifically to improvement in a surgical method for implanting an electrical sacral nerve stimulation lead in a living human patient for delivering electrical stimulation signals to the sacral nerves of the patient, for the treatment of incontinence and/or other medical conditions. The improvement comprises, first, locating the sacrum under the skin of the patient. Then, the soft tissues of the back of the living human patient are dilated from the skin above the sacrum to the sacrum through the introduction into the soft tissues of sequentially larger cannulated dilating devices, ending in a largest introduced dilating device. As more generally, a tubular retractor is inserted over the largest introduced dilating device and the dilating devices are retracted, thereby establishing an operative corridor through the dilated soft tissues to the foramen of the sacrum. The lead is inserted through the operative corridor to the foramen of the sacrum. The device is tested substantially in situ, and such other method steps are performed, including closing the operative corridor, as the implantation of the lead requires. Again, more specific steps of introducing an endoscope, testing, anchoring and the like may be included, as preferred.

BRIEF DESCRIPTION OF THE DRAWING

A drawing accompanies this specification, and includes a variety of figures. They are each briefly described as follows.

DETAILED DESCRIPTION OF THE PREFERRED EMBODIMENT

Figure 1:
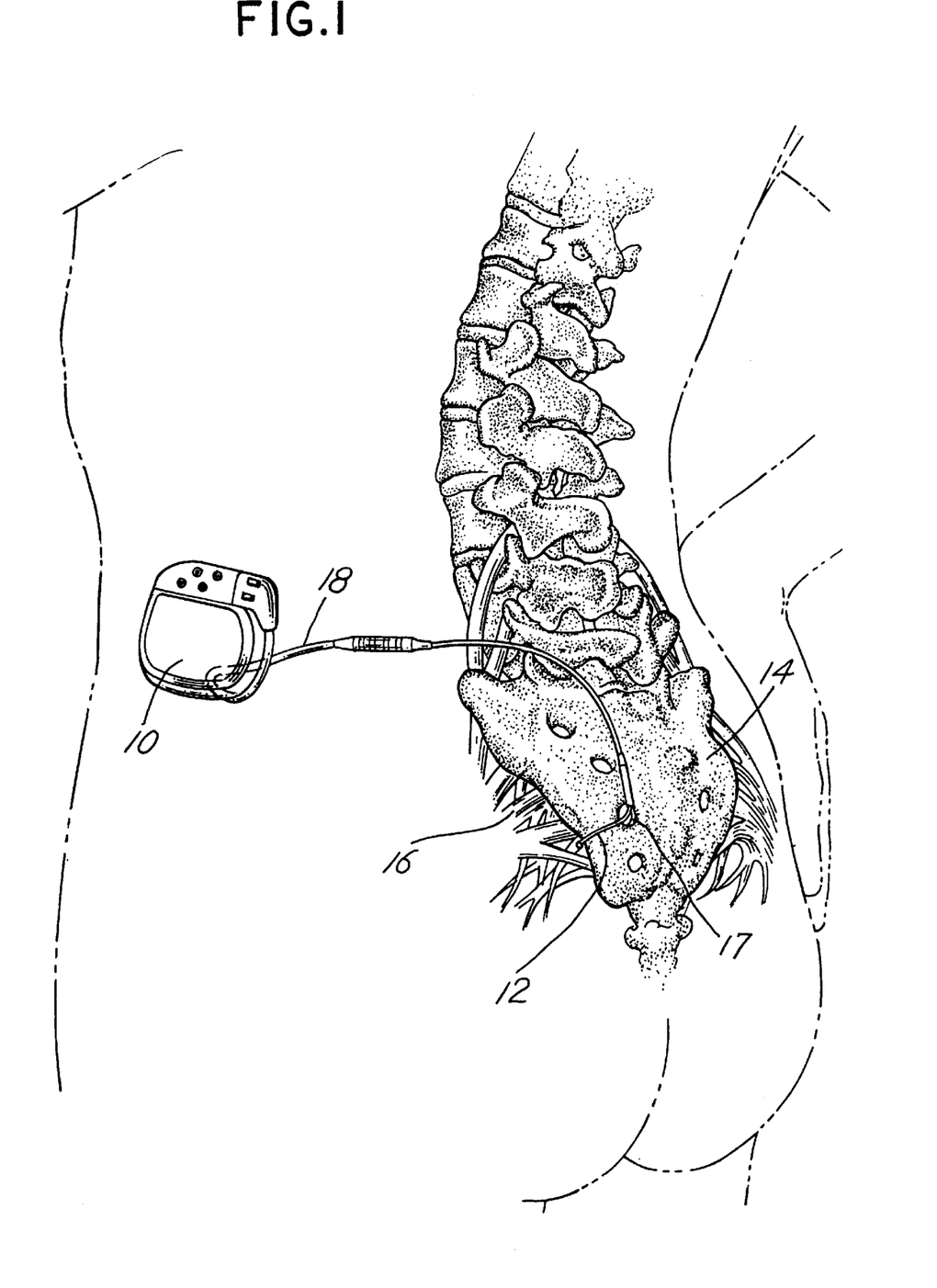
FIG. 1 is a diagrammatic view of a human patient in which a preferred form of nerve stimulation unit has been implanted for sacral nerve stimulation.

As referenced above, the currently available Medtronic InterStim® Therapy for Urinary Control offers an approach for managing urinary urge incontinence, nonobstructive urinary retention, and significant symptoms of urgency-frequency in patients who have failed or could not tolerate more conservative treatments. The implantable InterStim Therapy system uses mild electrical stimulation of the sacral nerves that influence the behavior of the bladder, sphincter, and pelvic floor muscles. Referring to FIG. 1, as with APT Neurostimulation, an IPG 10 contains a special battery and electronics to create electrical stimulation pulses. The IPG 10 is most often placed under the skin of the abdomen, as shown. The lead 12 is a small medical wire with special insulation. It is anchored to the sacrum 14 near the sacral nerves 16 and contains a set of electrodes (small electrical contacts)(see FIG. 3 and text below) through which electrical stimulation is delivered. This stimulation is often described as tingling. The extension 18 is a small cable between 4 to 20 inches long that is placed under the skin and connects the lead 12 to the IPG 10.

Figure 2:
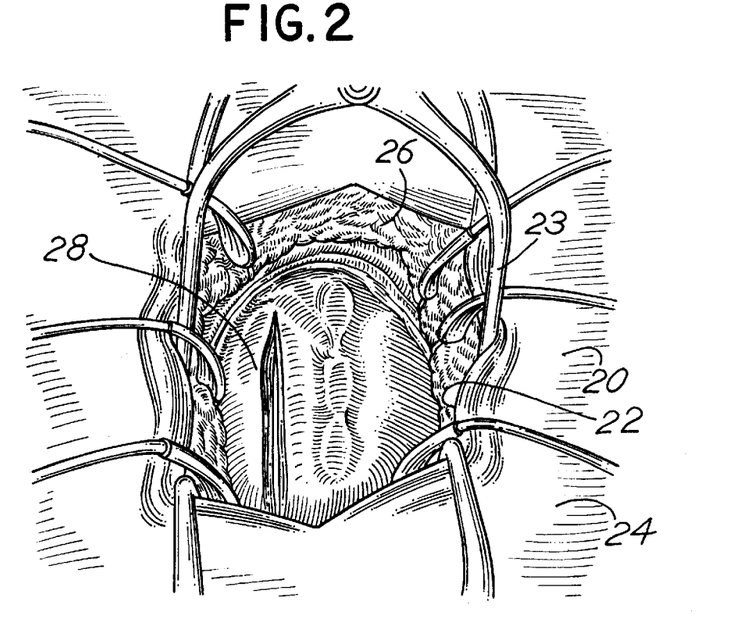
FIG. 2 is a view of a first stage of prior art surgery for implanting a lead for sacral nerve stimulation.
Figures 3, 4:
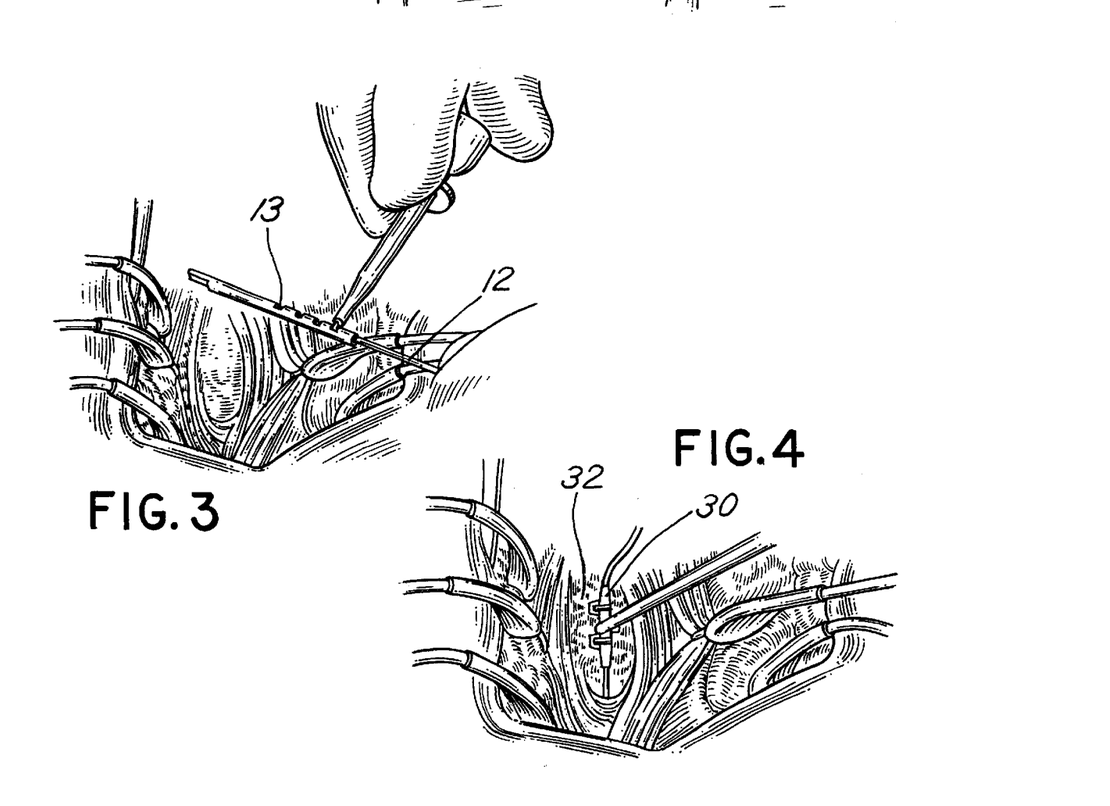
FIG. 3 is a view of a second stage of the prior art surgery.
FIG. 4 is a view of a third stage of the prior art surgery.
Figure 5:
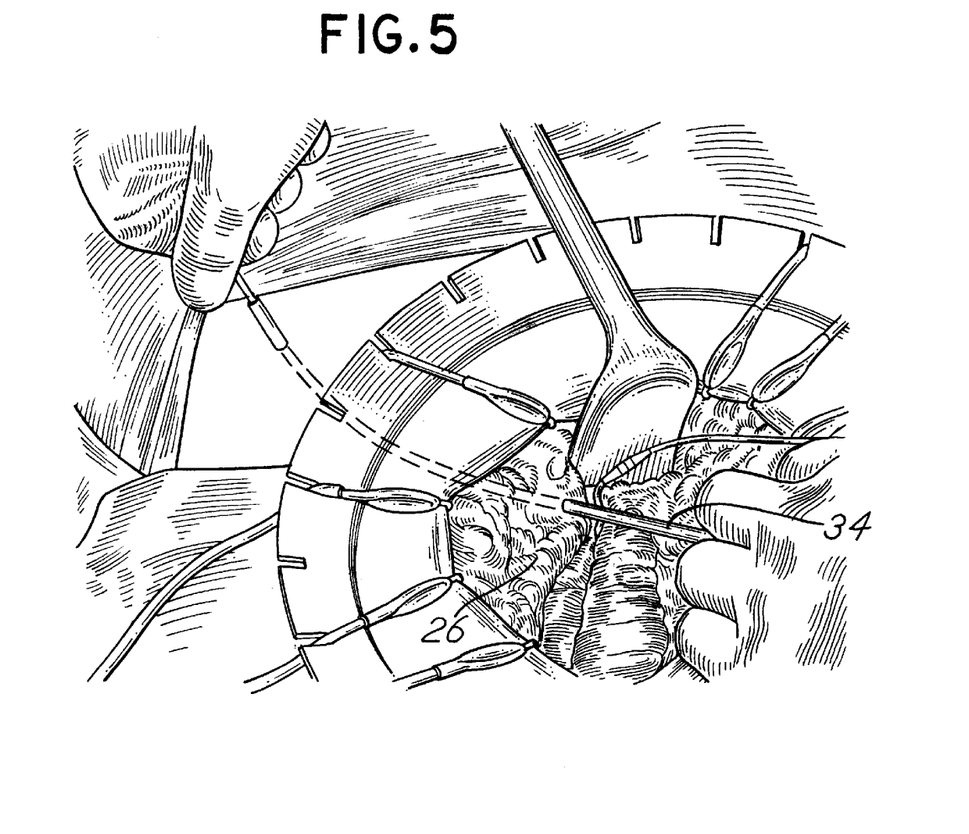
FIG. 5 is a view of a fourth stage of the prior art surgery.

As again in FIG. 1, for APT Medtronic InterStim® Therapy for Urinary Control, the lead 12 is placed through the dorsal (back) surface of the sacrum 14, the bone above the coccyx (tailbone) and below the last vertebrae, that forms the dorsal wall of the pelvis. The lead 12 is placed adjacent the sacral nerves 16 as they transition through the sacral foramina 17. As in FIG. 2, the human body 20 is opened to the sacrum 14 surgically. An incision 22 is made through the skin 24, fascia 26, and paraspinal muscle fibers 28. The incision is held open by retractors 23. The sacral foramina (foramen) 17 are exposed, preserving the periosteum (see FIG. 3 and text below). The response of the foramen 17 to stimulation is tested by a foramen needle (not shown). Once response is confirmed, the needle is retracted. Referring to FIG. 3, the lead 12 is tested outside the body for response. The lead 12 is then inserted into the foramen 17 to a depth of 1.0–1.5 inches in the usual case (see again FIG. 1). A lead anchor 30 is brought into contact with the periosteum 32, and the lead 12 is tested in situ on its various electrodes 13 for desired motor response. Once the desired response is observed, the lead 12 is anchored as in FIG. 4 by suturing the lead anchor 30 to the sacral bone or periosteum 32. As in FIG. 5, the fascia 26 of the sacral incision is closed. A tunneling tool 34 is then used to tunnel from the sacral site to a flank site (for abdominal IPG placement) and the extension 18 is placed to extend from the lead 12 to the IPG 10 (see again FIG. 1).

Consistent with current surgical technique, the invented improvement results in implantation of an electrical sacral nerve stimulation lead 12 in a living human patient for delivering electrical stimulation signals to the sacral nerves of the patient, for the treatment of incontinence and/or other medical conditions. The improvement comprises a variety of steps. As with the current method, the invented improvement begins with patient selection. Therapy is indicated for individuals who have failed or could not tolerate conservative therapies, including diet modification, physiotherapy, biofeedback, external electrical stimulation, anticholinergic agents, tricyclic antidepressants, antispasmodic agents, and augmentation intestinocystoplasty or urinary diversion, bladder denervation. A history is taken, a physical examination conducted, a culture done, the upper tract is evaluated, a cystoscopy conducted, a voiding diary kept and reviewed, a pelvic floor EMG completed, and a urodynamic evaluation accomplished to rule out treatable causes. The goal of any treatment for urge incontinence is to restore micturition, to prevent secondary health consequences, and to restore quality of life. Normal micturition relies on urine storage and release as reciprocal functions. The sacral nerves (S2, S3, and S4) stimulate—inhibit or facilitate—muscle function. The S3 nerve controls the two major muscles that must work together for continent urine storage and release.

Therapy efficacy for an implant as in the InterStim® Therapy for Urinary Control is tested using a temporary screening system before implant surgery is done. A test stimulation is conducted as an outpatient procedure. The purposes are to locate and identify the sacral nerves, verify the functional integrity of the nerves, allow the patient to feel the stimulation, and help the physician and patient make an informed choice. The patient is placed in a prone position and prepped. A ground pad is applied to the skin at a convenient location. The bony topography of the sacral area is palpated to find the sacral landmarks, or fluoroscopy is employed to the same effect. The sciatic notches are located, and on a finger width from the midline, the approximate sites of the S3 foramina are located. After an anesthetic is injected into the skin and subcutaneous layers and allowed to take effect, a foramen needle is inserted at an angle perpendicular to the bony surface. The rim of the foramen is palpated using needle sticks. The superior/inferior and medial/lateral margins are identified. The needle can be felt dropping through the foramen. The needle is connected to an electrical test stimulator. The amplitude of the test stimulator is turned on and increased to obtain sensory and/or motor response. Needle depth and/or angle are adjusted to find the best response.

A stylet is removed from the needle. A test stimulation lead is placed into the needle cannula. The foramen needle is removed. The test lead site is dressed, and the lead connected to the test stimulator. The patient is informed and educated, and for three to seven days, sent home. The stimulation should be felt at all times and feel comfortable. The patient may adjust intensity for optimum results, and vary frequency. The patient is to keep a voiding diary, and on return, the diary is evaluated for at least a 50% improvement in at least on of the following key symptom variables: number of leaking episodes per day, severity of leaking episodes, and number of pads and diapers replaced per day due to incontinence.

Figure 6:
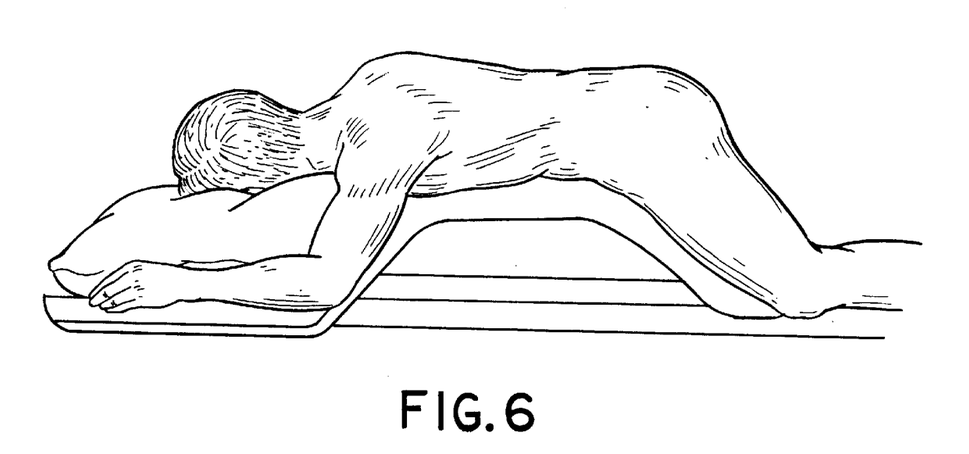
FIG. 6 is a diagrammatic view of a patient placed for sacral nerve implantation surgery.

If a more permanent implant is indicated, the procedure is begun. The patient is located as in FIG. 6. General anesthesia is administered. Muscle relaxants are contraindicated. The sacrum and perineum is prepared for sterile surgery. The test stimulation circumstances are reviewed, the sacral landmarks again located, and a foramen needle inserted as with the test stimulation. Re-testing should confirm the desired response. The foramen needle is then withdrawn.

Figure 7:
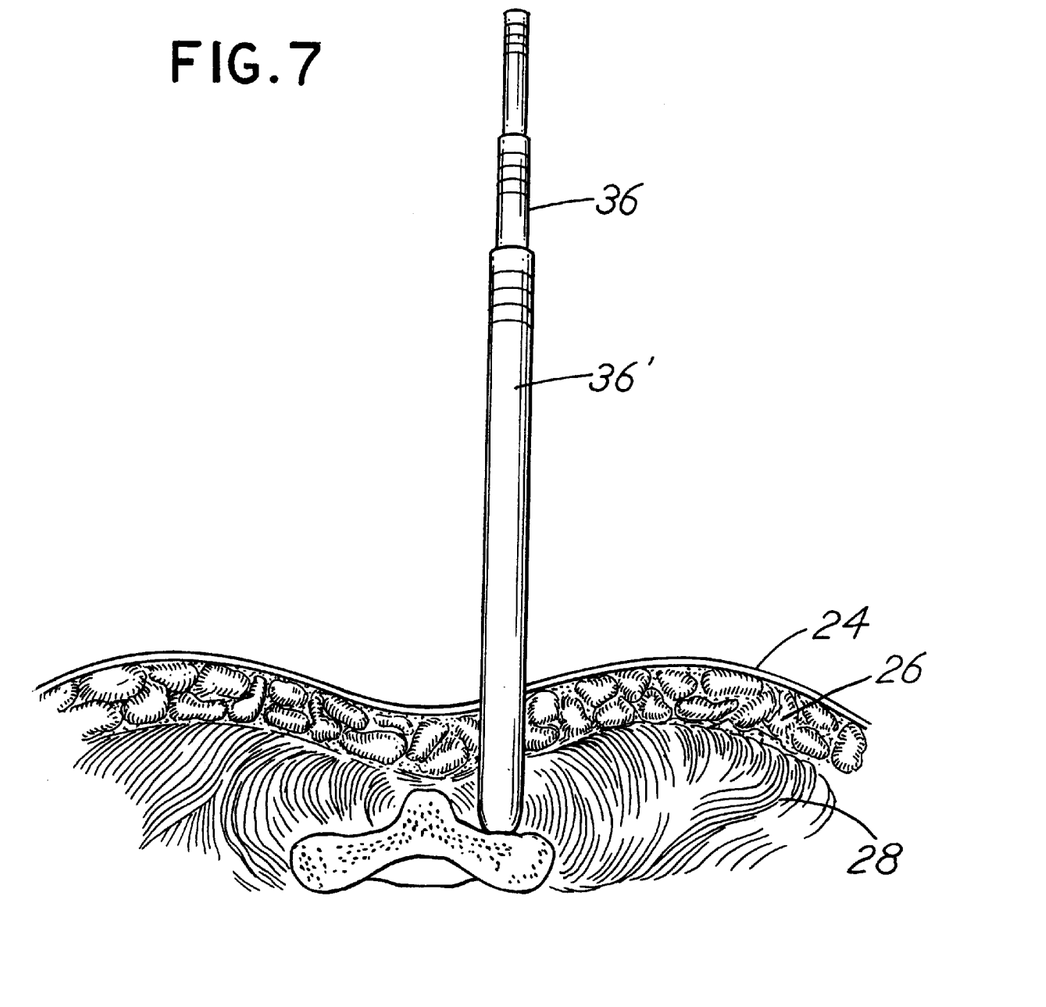
FIG. 7 is a view of a first stage of the invented surgical method.

Next, in contract with the current surgical method, as in FIG. 7, the soft tissues including the skin 24, fascia 26, and paraspinal muscles 28 of the lower back of the living human patient above the sacrum are dilated through the introduction into the soft tissues of sequentially larger cannulated dilating devices 36, ending in a largest introduced dilating device 36'.

Figure 8:
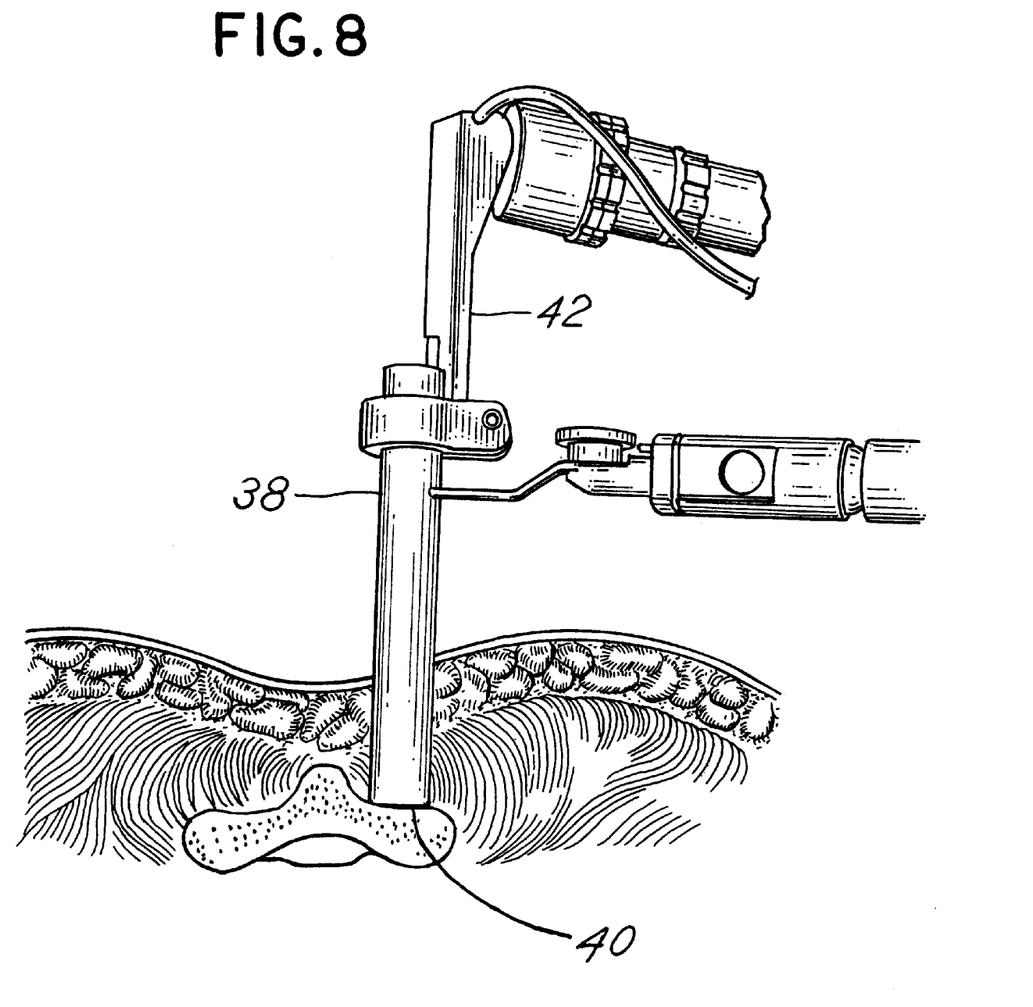
FIG. 8 is a view of a second stage of the invented surgical method.

A tubular retractor 38 is passed over the largest introduced dilating device 36'. The devices 36 are then retracted. As a result, an operative corridor 40 interior to the retractor 38 is defined through the dilated soft tissues to the foramen of the sacrum. As most preferred, the corridor is established sufficient in size for insertion of an endoscope to the site of sacrum.

Once the corridor 40 is defined, and again as most preferred, an endoscope 42 is inserted through the corridor 40 to adjacent the site of lead implantation. The endoscope 42 is utilized for visual imaging as needed during the remainder of the method.

The lead 12 is inserted through the operative corridor to the foramen of the sacrum. The lead 12 is tested in situ. Testing implements (not shown) are inserted and manipulated through the corridor for testing of the lead. Such other method steps are performed, including closing the operative corridor, as the implantation of the lead requires. As an example, the lead is anchored at the site of implantation through insertion and manipulation of anchoring implements through the corridor before closing the corridor.

After closing the sacral incision site partially, by partial retraction of the tubular retractor, a subcutaneous tunnel is created to the flank site, the site of implantation of the IPG. A tunneling tip is attached to a tunneling tool. The tool is bent for insertion into the body, and re-bent progressively as tunneling continues. The tunneling tip is removed, leaving a tube. The lead is suctioned or fed through the tube. The site is completely closed.

The patient is rotated, re-prepped, and a pocket create by blunt dissection for the IPG. The IPG is checked for fit in the pocket. The flank site is connected to the IPG site by further tunneling for the extension. The lead and extension are connected. The extension and IPG are connected. The IPG is placed in its pocket, and secured. The flank site and IPG pocket are closed, and implantation documented.

Post-operative procedures occur after the patient is awake and comfortable. Patients can be released once they meet standard hospital discharge protocol, and the following criteria: awareness of sacral stimulation that is not painfull when initiated at the hospital, and a proper understanding of the system. The IPG can be non-invasively programmed.

The patient uses a control magnet to toggle the IPG between on and off. When off, voiding occurs. When on, low voltage electricity produces a modulating effect on the detrusor muscle of the bladder, stopping voiding.

For this specification, the term "stimulant" includes both electrical stimulation signals and drugs. The term "central nervous system" includes the spinal cord and/or peripheral nerves. Details of a variety of aspects of the invented procedure are consistent with past medical practice, and explained in a variety of Medtronic publications, including its Interstim® Continence Control Therapy Test Stimulation and Implantation Guide, incorporated by reference.

The preferred embodiments of the invention, and the invention itself, are now described in such full, clear, concise and exact terms as to enable a person of ordinary skill in the art to make and use the invention. To particularly point and distinctly claim the subject matters regarded as invention, the following claims conclude this specification. To the extent variations from the preferred embodiments fall within the limits of the claims, they are considered to be part of the invention, and claimed.

What is claimed is:

1. In a surgical method for implanting a device in a living body for delivering a stimulant to the nervous system of the body, the improvement comprising:

dilating the soft tissues of the body at a site of device implantation to create dilated soft tissues, through the introduction into the soft tissue of sequentially larger cannulated dilating devices, ending in a largest introduced dilating device;

passing a tubular retractor over the largest introduced dilating device and retracting a number of the dilating devices, thereby establishing a tubular device insertion corridor through the dilated soft tissues to the site of device implantation;

inserting the device to be implanted through the operative corridor to the site of device implantation;

testing the device to be implanted substantially in situ; and closing the operative corridor.

2. In a surgical method for implanting a device in a living body for delivering a stimulant to the nervous system of the body, the improvement of claim 1 further comprising:

when retracting a number of the dilating devices, retracting all the dilating devices.

3. In a surgical method for implanting a device in a living body for delivering a stimulant to the nervous system of the body, the improvement of claim 1 further comprising:

when establishing a tubular device insertion corridor through the dilated tissues to the site of device implantation, establishing a corridor sufficient in size for insertion of an endoscope to the site of device implantation;

inserting the endoscope through the corridor to adjacent the site of device implantation; and utilizing the endoscope for visual imaging as needed during the method.

4. In a surgical method for implanting a device in a living body for delivering a stimulant to the nervous system of the body, the improvement as in claim 1 further comprising:

testing the nervous system of the body for appropriate reaction to the stimulant through insertion and manipulation of testing implements through the corridor before testing the device and before performing other method steps.

5. In a surgical method for implanting a device in a living body for delivering a stimulant to the nervous system of the body, the improvement as in claim 1 further comprising:

anchoring the device at the site of device implantation through insertion and manipulation of anchoring implements through the corridor before closing the corridor.

6. In a surgical method for implanting an electrical stimulation lead in a living body for delivering electrical stimulation to the nervous system of the body, the improvement comprising:

dilating the soft tissues of the body at the site of lead implantation to create dilated soft tissues, through the introduction into the tissue of sequentially larger cannulated dilating devices, ending in a largest introduced dilating device;

passing a tubular retractor over the largest introduced dilating device and retracting a number of the dilating devices, thereby establishing a tubular lead insertion corridor through the dilated tissues to the site of lead implantation;

inserting the lead through the operative corridor to the site of lead implantation;

testing the lead substantially in situ; and closing the operative corridor.

7. In a surgical method for implanting an electrical stimulation lead in a living body for delivering electrical stimulation to the nervous system of the body, the improvement of claim 6 further comprising:

when retracting a number of the dilating devices, retracting all the dilating devices.

8. In a surgical method for implanting an electrical stimulation lead in a living body for delivering electrical stimulation to the nervous system of the body, the improvement of claim 6 further comprising:

when establishing a tubular device insertion corridor through the dilated tissues to the site of lead implantation, establishing a corridor sufficient in size for insertion of an endoscope to the site of lead implantation;

inserting the endoscope through the corridor to adjacent the site of lead implantation; and utilizing the endoscope for visual imaging as needed during the method.

9. In a surgical method for implanting an electrical stimulation lead in a living body for delivering electrical stimulation to the nervous system of the body, the improvement of claim 6 further comprising:

testing the nervous system of the body for appropriate reaction to the electrical stimulation through insertion and manipulation of testing implements through the corridor before testing the lead and before performing other method steps.

10. In a surgical method for implanting an electrical stimulation lead in a living body for delivering electrical stimulation to the nervous system of the body, the improvement of claim 6 further comprising:

anchoring the lead at the site of lead implantation through insertion and manipulation of anchoring implements through the corridor before closing the corridor.

11. In a surgical method for implanting an electrical sacral nerve stimulation lead in a living human patient for delivering electrical stimulation signals to the sacral nerves of the patient, for the treatment of incontinence and/or other medical conditions, the improvement comprising:

locating the sacrum under the skin of the patient;

dilating the soft tissues of the back of the living human patient from the skin above the sacrum to the sacrum through the introduction into the soft tissues of sequentially larger cannulated dilating devices, ending in a largest introduced dilating device;

passing a tubular retractor over the largest introduced dilating device and retracting the dilating devices, thereby establishing an operative corridor through the dilated soft tissues to the foramen of the sacrum;

inserting the lead through the operative corridor to the foramen of the sacrum;

testing the device substantially in situ; and closing the operative corridor.

12. In a surgical method for implanting an electrical sacral nerve stimulation lead in a living human patient for delivering electrical stimulation signals to the sacral nerves of the patient, for the treatment of incontinence and/or other medical conditions, as in claim 11, the improvement comprising:

when retracting a number of the dilating devices, retracting all the dilating devices.

13. In a surgical method for implanting an electrical sacral nerve stimulation lead in a living human patient for delivering electrical stimulation signals to the sacral nerves of the patient, for the treatment of incontinence and/or other medical conditions, as in claim 11, the improvement comprising:

when establishing an operative corridor through the dilated tissues to the site of lead implantation, establishing a corridor sufficient in size for insertion of an endoscope to the site of lead implantation;

inserting the endoscope through the corridor to adjacent the site of lead implantation; and utilizing the endoscope for visual imaging as needed during the method.

14. In a surgical method for implanting an electrical sacral nerve stimulation lead in a living human patient for delivering electrical stimulation signals to the sacral nerves of the patient, for the treatment of incontinence and/or other medical conditions, as in claim 11, the improvement comprising:

testing the sacral nerves for appropriate reaction to the electrical stimulation through insertion and manipulation of testing implements through the corridor before testing the lead and performing other steps.

15. In a surgical method for implanting an electrical sacral nerve stimulation lead in a living human patient for delivering electrical stimulation signals to the sacral nerves of the patient, for the treatment of incontinence and/or other medical conditions, as in claim 11, the improvement comprising:

anchoring the lead at the site of implantation through insertion and manipulation of anchoring implements through the corridor before closing the corridor.

* * * * *